US009884166B2

(12) United States Patent
Howle et al.

(10) Patent No.: US 9,884,166 B2
(45) Date of Patent: Feb. 6, 2018

(54) JETLESS INTRAVENOUS CATHETERS AND MECHANICAL ASSIST DEVICES FOR HAND-INJECTION OF CONTRAST MEDIA DURING DYNAMIC TOMOGRAPHY AND METHODS OF USE

(75) Inventors: Laurens E. Howle, Mebane, NC (US); Rendon Nelson, Durham, NC (US); Eli Nichols, Durham, NC (US); Sebastian T. Schindera, Basel (CH); Courtney Coursey, Atlanta, GA (US); Paul W. Weber, Vienna, VA (US)

(73) Assignee: Duke University, Durham, NC (US)

( * ) Notice: Subject to any disclaimer, the term of this patent is extended or adjusted under 35 U.S.C. 154(b) by 972 days.

(21) Appl. No.: 13/574,705

(22) PCT Filed: Jan. 21, 2011

(86) PCT No.: PCT/US2011/022088
§ 371 (c)(1),
(2), (4) Date: Jun. 17, 2013

(87) PCT Pub. No.: WO2011/091275
PCT Pub. Date: Jul. 28, 2011

(65) Prior Publication Data
US 2013/0267845 A1    Oct. 10, 2013

Related U.S. Application Data

(60) Provisional application No. 61/297,758, filed on Jan. 23, 2010, provisional application No. 61/353,811, filed on Jun. 11, 2010.

(51) Int. Cl.
*A61M 25/00*    (2006.01)
*A61M 31/00*    (2006.01)
(Continued)

(52) U.S. Cl.
CPC ........ *A61M 25/0068* (2013.01); *A61M 5/007* (2013.01); *A61M 25/007* (2013.01);
(Continued)

(58) Field of Classification Search
CPC ............ A61M 25/007; A61M 25/0015; A61M 25/0068; A61M 5/007; A61M 5/14546;
(Continued)

(56) References Cited

U.S. PATENT DOCUMENTS 3,111,059 A    11/1963    Marsh
5,800,407 A *  9/1998    Eldor .................. A61M 25/007
                                                        604/264
(Continued)

FOREIGN PATENT DOCUMENTS

WO    WO 2008/067362 A2    6/2008
WO    WO 2008067362 A2 *  6/2008 .......... A61M 25/007
WO    WO 2008/085421 A2    7/2008

OTHER PUBLICATIONS

Transmittal of International Preliminary Report on Patentability, dated Aug. 2, 2012.
(Continued)

*Primary Examiner* — Timothy J Neal
(74) *Attorney, Agent, or Firm* — Myers Bigel, P.A.

(57) ABSTRACT

A jetless intravenous catheter for the delivery of a fluid into a peripheral vein of a subject includes an elongated body having proximal and distal ends. The body includes a wall defining an internal fluid passageway configured to receive fluid flowing in a longitudinal direction from the proximal end at a first axial velocity and a tip aperture at the distal end configured to allow fluid to exit therethrough. The body comprises at least one flow reducing feature configured to create a laminar-turbulent transitional flow associated with a fluid flowing in the longitudinal direction at the first axial
(Continued)

velocity and configured to reduce the flow velocity of fluid exiting the tip to a second axial velocity that is less than the first axial velocity.

23 Claims, 10 Drawing Sheets

(51) Int. Cl.
    *A61M 5/00* (2006.01)
    *A61M 5/145* (2006.01)
(52) U.S. Cl.
    CPC ......... *A61M 31/005* (2013.01); *A61M 5/1456* (2013.01); *A61M 5/14546* (2013.01); *A61M 2025/006* (2013.01); *A61M 2025/0073* (2013.01); *A61M 2206/11* (2013.01); *A61M 2206/20* (2013.01)
(58) Field of Classification Search
    CPC .............. A61M 5/1456; A61M 31/005; A61M 2025/0057
    USPC .................................. 600/118, 153–159, 432
    See application file for complete search history.

(56) References Cited

U.S. PATENT DOCUMENTS

| | | | |
|---|---|---|---|
| 6,117,125 A * | 9/2000 | Rothbarth | A61M 25/007 604/264 |
| 6,213,978 B1 * | 4/2001 | Voyten | A61M 25/0606 604/164.01 |
| 6,626,885 B2 * | 9/2003 | Massengale | A61M 25/0043 604/508 |
| 7,066,917 B2 * | 6/2006 | Talamonti | A61M 1/0058 604/276 |
| 2002/0198550 A1 | 12/2002 | Nash et al. | |
| 2004/0039351 A1 * | 2/2004 | Barrett | A61M 1/008 604/272 |
| 2004/0054278 A1 | 3/2004 | Kimchy et al. | |
| 2005/0171510 A1 * | 8/2005 | DiCarlo | A61M 39/24 604/537 |
| 2007/0142817 A1 * | 6/2007 | Hurt | A61M 25/007 604/508 |
| 2008/0045925 A1 | 2/2008 | Stepovich et al. | |
| 2008/0064920 A1 | 3/2008 | Bakos et al. | |
| 2008/0294096 A1 | 11/2008 | Uber, III et al. | |
| 2009/0118661 A1 * | 5/2009 | Moehle | A61M 25/0068 604/6.16 |
| 2009/0177050 A1 | 7/2009 | Griffiths et al. | |
| 2009/0254062 A1 * | 10/2009 | McGlothlin | A61M 25/0015 604/508 |
| 2009/0287186 A1 | 11/2009 | Adams et al. | |
| 2010/0069836 A1 * | 3/2010 | Satake | A61B 18/10 604/96.01 |
| 2011/0144429 A1 * | 6/2011 | Finkman | A61B 1/00091 600/104 |

OTHER PUBLICATIONS

Partial Supplementary European Search Report for EP Application No. 11735242.7 dated Sep. 26, 2017, 11 pages.

* cited by examiner

150

… (1) …

JETLESS INTRAVENOUS CATHETERS AND MECHANICAL ASSIST DEVICES FOR HAND-INJECTION OF CONTRAST MEDIA DURING DYNAMIC TOMOGRAPHY AND METHODS OF USE

RELATED APPLICATIONS

This application is a 35 U.S.C. §371 national phase application of PCT International Application No. PCT/US2011/022088, filed Jan. 21, 2011, which claims priority from U.S. Provisional Patent Application No. 61/297,758, filed Jan. 23, 2010, and from U.S. Provisional Patent Application No. 61/353,811, filed Jun. 11, 2010, the disclosures of which are hereby incorporated herein in their entireties.

FIELD OF THE INVENTION

This invention relates to intravenous catheters and computer tomography and, more particularly, to jetless intravenous catheters and mechanical assist devices for hand-injection of contrast media during computer tomography, as well as methods of using the same.

BACKGROUND

Computer tomography (CT) is a high resolution imaging technique that has relatively low inherent contrast resolution in soft tissue structures such as the liver, spleen, pancreas and kidneys. More than 62 million CT scans are performed each year in the United States in about 7,200 facilities, and approximately 40 million of these procedures require the intravenous administration of iodinated contrast material. In order to be effective, the iodinated contrast material is administered intravenously as a bolus infusion (not a drip infusion) for most clinical indications. The exceptions would include the search for acute hemorrhage or calculi, particularly in the genitourinary tract, when intravenous contrast material is not necessary and in some cases contraindicated.

When administering iodinated contrast material as a bolus, it is typically delivered via a power injector that is programmed prior to the CT acquisition. That is, the volume, rate and pressure of administration are preset before delivering the contrast material and subsequently acquiring the CT scan. For example, 150 ml of a contrast agent would be administered at 5 ml/sec with a maximum pressure of 300 pounds per square inch (PSI). However, in some cases, the use of a power injector results in the extravasation of the iodinated contrast compound (i.e., leakage outside the vein into the surrounding soft tissue). Such incidents result in unreliable and/or ineffective CT scans as well as adverse effects on the patient, such as skin ulcerations and compartment syndrome, which require additional medical attention.

Although some power injectors use devices to detect the extravasation of contrast material (e.g., EZ-EM, MedRad), the technologists or nurses responsible for administering the contrast media bolus frequently encounter a scenario where they are uncomfortable or wary of using the power injector. Typical scenarios that may be problematic include: (1) poor or tenuous intravenous access; (2) use of an existing IV line in an in-patient that has been in place for several days; (3) injection of a central venous catheter through which many hospitals have policies prohibiting power injection; and (4) injection of children. When one or more of these scenarios occurs, contrast material is typically administered via a hand injection. That is, the technologist or nurse administers the contrast material by hand with one or more syringes. Since the volumes of contrast material used for CT are typically in the 125-150 ml range, and because larger volume syringes require more force to push the plunger, the contrast material is typically divided up into several smaller syringes. For example, rather than injecting 150 ml of contrast material via a 150 ml syringe, the technologist or nurse may inject 25 ml through six different 25 ml syringes. This problem is further exacerbated by the fact that contrast agents with higher concentrations of iodine (e.g., 370 mg/ml rather than 300 mg/ml) are becoming increasingly popular in the era of fast, multidetector CT scanners. The contrast agents with higher concentrations of iodine have a much higher viscosity, making them even more difficult to inject by hand. Although administering the bolus via several small volume syringes is much easier for the individual performing the injection, the episodic delivery of contrast material (e.g., inject 25 ml, disconnect the empty syringe, reconnect a full syringe, inject more contrast material, etc.) results in a suboptimal vascular and tissue enhancement profile.

This administration scheme is not compatible with the goal of having vivid and sustained vascular and tissue enhancement during the CT acquisition. As a result, certain subtle but critical disease processes such as hepatic, pancreatic or renal tumors may be missed. Furthermore, other protocols such as CT angiography cannot be performed using a hand injection, since certain diagnoses, such as pulmonary embolism, rely on very vivid vascular enhancement. In summary, the use of hand injection reduces the risk of contrast media extravasation into the perivenous soft tissue but results in a suboptimal CT scan from a diagnostic standpoint.

Moreover, the catheters currently used to inject the contrast media in the patient can cause extravasation. As described above, because the contrast media must be administered as a bolus, these catheters produce a jet at the catheter tip, which can result in extravasation of the contrast media into the surrounding soft tissue of the patient. For example, vessel wall perforation may be caused by the contrast media jet exiting the aperture at the tip of a typical catheter. For this reason, the flow rate of the contrast media may have to be reduced, requiring a longer time to deliver the fluid.

The present disclosure addresses these current problems in the field of computer tomography imaging.

SUMMARY

As a first aspect, embodiments of the present invention are directed to a jetless intravenous catheter for the delivery of a fluid into a peripheral vein of a subject. The jetless catheter includes an elongated body having proximal and distal ends. The body includes a wall defining an internal fluid passageway configured to receive fluid flowing in a longitudinal direction from the proximal end at a first axial velocity and a tip aperture at the distal end configured to allow fluid to exit therethrough. The body comprises at least one flow reducing feature configured to create a laminar-turbulent transitional flow associated with a fluid flowing in the longitudinal direction at the first axial velocity and configured to reduce the flow velocity of fluid exiting the tip to a second axial velocity that is less than the first axial velocity.

The flow reducing feature may comprise a plurality of apertures in the wall such that a portion of a fluid flowing in the longitudinal direction exits the body through the plurality of apertures.

In some embodiments, the plurality of apertures may comprise a plurality of substantially circular spaced-apart holes. The plurality of holes may be located between about 3 mm and about 10 mm from the distal end. Each of the plurality of holes may have a diameter of at least about 100 µm.

The plurality of holes may comprise a first row of spaced-apart holes aligned in the longitudinal direction on a first side of the body and a second row of spaced-apart holes aligned in the longitudinal direction on a second, diametrically opposed side of the body. The plurality of holes may comprise a third row of spaced-apart holes aligned in the longitudinal direction on a top side of the body. Each of the first and second rows of holes may include a first hole closest to the distal end that has a first diameter, a second hole furthest from the distal end that has a second diameter that is greater than or less than the first diameter, and a third hole positioned between the first and second holes that has a third diameter that is between the first and second diameters.

In some embodiments, the plurality of apertures comprises a plurality of elongated slits extending in the longitudinal direction. Each slit may have a length of about 2.5 mm. The plurality of slits may include at least one slit on a top of the body and at least one slit on each of diametrically opposed sides of the body. The plurality of slits may be staggered such that the slit on the top of the body extends closer to the distal end of the body than the slits on the diametrically opposed sides of the body. Each slit may be tapered in the longitudinal direction such that the slit narrows as the slit extends away from the distal end of the body.

The flow reducing feature may be configured to excite the laminar-turbulent transition instability associated with a fluid flowing in the longitudinal direction.

In some embodiments, the jetless catheter includes a hub connectable to the proximal end of the body, the hub having an interior cavity with at least one vorticity introducing feature configured to introduce vorticity to fluid flowing therethrough and into the fluid passageway of the body. The at least one vorticity introducing feature of the hub may comprise at least one groove and/or at least one fin. The at least one vorticity introducing feature of the hub may comprise at least one vibrating fin.

In some embodiments, the jetless catheter further comprises a stylet positioned within the internal fluid passageway, the stylet having a beveled distal end that extends past the distal end of the body. The stylet distal end may extend about 2 mm past the distal end of the body.

As a second aspect, an intravenous catheter for the delivery of a fluid into a peripheral vein of a subject includes an elongated body having proximal and distal ends. The body includes a wall defining an internal fluid passageway configured to receive fluid flowing in a longitudinal direction from the proximal end and a tip including an aperture at the distal end configured to allow fluid to exit therethrough. The body comprises at least one fluid dispersing feature configured to rapidly disperse a fluid jet associated with a fluid flowing in the longitudinal direction as the fluid exits the tip aperture.

In some embodiments, the fluid dispersing feature comprises an at least partially beveled tip including an opening toward the top of the body. In some embodiments, the fluid dispersing feature comprises at least one groove in an interior of the wall, the at least one groove helically disposed in the wall along the longitudinal direction. The at least one groove may comprise a plurality of grooves, the grooves configured to create vorticity in a fluid flowing in the longitudinal direction.

As a third aspect, a mechanical assist device for hand-injection of contrast media during dynamic tomography is provided. The assist device includes a base. A compartment at a top of the base is sized and configured to securely hold at least a portion of a syringe. A plate extends upwardly from the top of the base, and the plate is sized and configured to receive a plunger of a syringe securely held in the compartment. The plate is slidably moveable in a first direction from a first position away from the compartment to a second position adjacent the compartment. A hand-operated actuator is in communication with the plate, wherein the plate slidably moves in the first direction in response to actuation of the actuator. When a syringe is securely held in the compartment, the plate slidably moves the plunger of the syringe from the first position to the second position at a substantially constant rate such that fluid exits the syringe at a substantially constant rate in response to actuation of the actuator.

The base top may include a slot through which the plate extends and along which the plate slidably moves in the first direction.

In some embodiments, the assist device comprises a monitoring device for monitoring the rate at which fluid exits the syringe body. The monitoring device may be a dial or a digital display attached to the base.

The actuator may be a rotatable crank. A drive mechanism may be provided and configured to convert rotational motion of the crank into translational motion of the plate such that the plate slidably moves in the first direction in response to rotation of the crank.

In some embodiments, a bottom of the base is configured to be attached to a scanner table.

In some embodiments, the assist device is configured to deliver at least 125 ml of contrast media at a substantially constant rate of at least 5 ml/sec. In some embodiments, the contrast media has an iodine concentration of at least 300 mg/ml.

As a fourth aspect, a method for assisting the hand-injection of contrast media during computer tomography (CT), comprises: (a) providing a mechanical assist device including: a compartment sized and configured to securely hold at least a portion of a syringe; a plate sized and configured to receive a plunger of a syringe securely held by the compartment, the plate slidably movable in a first direction from a first position away from the compartment to a second position adjacent the compartment; and a hand-operated actuator in communication with the plate such that the plate is slidable in the first direction in response to actuation of the actuator; (b) positioning a syringe containing contrast media such that at least a portion of the syringe is securely held by the compartment and a plunger of the syringe is received by the plate in the first position; (c) actuating the actuator to move the plate and plunger in the first direction; and (d) maintaining a substantially constant injection rate of contrast media from the syringe.

In some embodiments, the following are the following are performed prior to the actuating step: (a) establishing an intravenous line to a subject at an injection site; (b) connecting the syringe to the intravenous line. In some embodiments, the method further comprises monitoring the injection site using finger palpation during the actuating step. The maintaining step may comprise monitoring a device configured to monitor media flow.

In some embodiments, the syringe contains a volume at least 100 ml of contrast media that has an iodine concentration of at least 300 mg/ml, and the maintaining step comprises maintaining a constant injection rate of at least 5 ml/sec from the syringe.

As a fifth aspect, an assembly for assisting the rapid hand injection of contrast media into a peripheral vein of a subject and minimizing a jet of contrast media into the peripheral vein during computer tomography is provided. The assembly includes a syringe having a body, a plunger, and a tip, with the syringe containing at least 100 ml of contrast media having an iodine concentration of at least 300 mg/ml. The assembly also includes a mechanical assist device, comprising: (a) a base; (b) a compartment at a top of the base sized and configured to securely hold the body of the syringe; (c) a plate extending upwardly from the top of the base, the plate sized and configured to receive the plunger of the syringe securely held in the compartment, the plate slidably moveable in a first direction from a first position away from the compartment to a second position adjacent the compartment; and (d) a hand-operated actuator in communication with the plate, wherein the plate slidably moves in the first direction in response to actuation of the actuator. When the syringe body is securely held in the compartment, the plate slidably moves the plunger of the syringe from the first position to the second position at a substantially constant rate such that the contrast media exits the tip of the syringe at a substantially constant rate of at least 5 ml/sec in response to actuation of the actuator. The assembly also includes a catheter in fluid communication with the tip of the syringe, the catheter comprising: an elongated body having proximal and distal ends, the body including a wall defining an internal fluid passageway configured to receive the contrast media flowing from the syringe tip in a longitudinal direction from the proximal end at a first axial velocity and a tip aperture at the distal end configured to allow the contrast media to exit therethrough. The body comprises at least one flow reducing feature configured to create a laminar-turbulent transitional flow associated with the contrast media flowing in the longitudinal direction at the first axial velocity and configured to reduce the flow velocity of the contrast media exiting the tip to a second axial velocity that is less than the first axial velocity.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION OF EMBODIMENTS OF THE INVENTION

Figure 1:
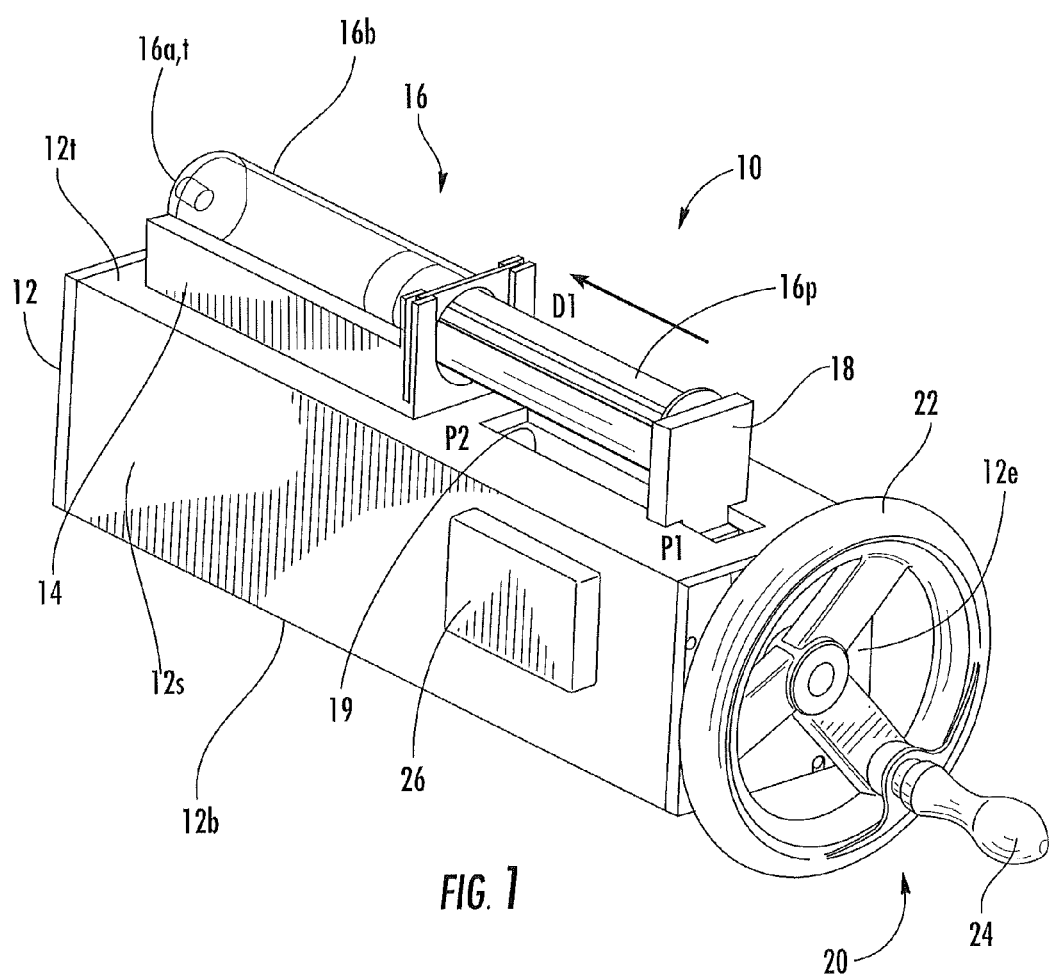
FIG. 1 is a perspective view of a mechanical assist device for hand-injection of contrast media during dynamic computer tomography according to some embodiments of the invention.

The present invention will be described more particularly hereinafter with reference to the accompanying drawings. The invention is not intended to be limited to the illustrated embodiments; rather, these embodiments are intended to fully and completely disclose the invention to those skilled in this art. In the drawings, like numbers refer to like elements throughout. Thicknesses and dimensions of some components may be exaggerated for clarity.

Well-known functions or constructions may not be described in detail for brevity and/or clarity.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. As used herein, the term "and/or" includes any and all combinations of one or more of the associated listed items. Where used, the terms "attached," "connected," "interconnected," "contacting," "coupled," "mounted," "overlying" and the like can mean either direct or indirect attachment or contact between elements, unless stated otherwise.

Referring now to the figures, a mechanical assist device for the hand-injection of contrast media during dynamic computer tomography (CT), designated broadly at 10, is illustrated in FIG. 1. The device includes a base 12 having a top 12t. A compartment 14 is attached to or integrally formed with the top 12t of the base 12. The compartment 14 is sized and configured to receive and securely hold at least a portion of a syringe 16. As illustrated, the compartment 14 is configured to securely hold a body 16b of the syringe 16. In various embodiments, the compartment may be configured to securely hold a syringe having a volume of between about 100 ml to about 500 ml, between about 110 ml to about 400 ml, between about 115 ml to about 300 ml, between about 120 ml to about 200 ml, and between about 125 ml to about 175 ml.

A plate 18 extends upwardly from the top 12t of the base 12. The plate 18 is sized and configured to receive a plunger 16p of the syringe 16 (more particularly, the plate 18 may be sized and configured to receive a plunger handle or head, as illustrated). The plate 18 is slidably moveable in a first longitudinal direction D1 from a first position P1 located away from the compartment 14 to a second position P2 adjacent the compartment 14. As illustrated, the base top 12t includes a slot 19 through which the plate 18 extends upwardly and along which the plate 18 slidably moves in the first direction D1. The plate 18 is also slidably moveable in the opposite longitudinal direction (i.e., from position P2 to position P1).

A hand-operated actuator 20 is in communication with the plate 18. The plate 18 slidably moves in the first direction D1 in response to actuation of the actuator 20. In the illustrated embodiment, the actuator 20 is a crank that includes a rotatable wheel 22 that can be turned by a handle 24. It will be understood that the actuator 20 may alternatively be a lever or some other hand-operated actuator.

In some embodiments, the base 12 can take the form of a housing, and can include a bottom 12b, opposing side walls 12s, and opposing end walls 12e. In this regard, the base 12 may include an at least partially open interior (not visible in FIG. 1), and a drive mechanism (also not visible) may be positioned therein and may couple the plate 18 and the actuator 20. For example, the drive mechanism may convert rotational motion of the crank 20 into translational motion of the plate 18 such that the plate 18 slidably moves in the first direction D1 responsive to rotation of the crank 20. The plate 18 may slidably move in the first direction D1 responsive to rotation of the crank in one direction (e.g., counterclockwise), and may slidably move in the opposite direction responsive to rotation of the crank 20 in the opposite direction (e.g., clockwise). As will be understood by those of skill in the art, the drive mechanism may take the form of a rack and pinion, a jack screw, or the like.

In operation, the syringe 16 is securely held in the compartment 14, and the plate 18 slidably moves the plunger 16p in the first direction D1 from the first position P1 to the second position P2 in response to actuation of the actuator 20. As the plunger 16p enters the syringe body 16b, fluid held in the body 16b is forced therefrom through an aperture 16a at a tip 16t of the syringe 16. High pressure tubing may be used to connect the tip 16t to an intravenous (IV) line such as a catheter.

The actuator 20 provides leverage such that a user can slidably move the plate 18 from the first position P1 to the second position P2 at a substantially constant rate and/or a relatively rapid rate. In this regard, the entire volume or substantially the entire volume of fluid held in the body of the syringe can exit therefrom at a substantially constant rate and/or a relatively rapid rate responsive to actuation of the actuator. In particular, the device 10 can assist the hand-injection of a relatively large volume (e.g., at least 100 or 150 ml) of relatively viscous contrast material (e.g., iopamidol 300 mg iodine/ml or iopamidol 370 mg iodine/ml) at a substantially constant and relatively rapid rate (e.g., 5 or 10 ml/sec). It will be understood that the device 10 may be used to assist the hand-injection of lesser volumes of fluid, such as at least 25 ml (a lesser volume may be required for certain procedures, such as MR). A lower flow rate (e.g., 2 ml/sec) could also be employed.

The device 10 may include a monitoring device 26 for monitoring the pressure or rate at which contrast material exits the syringe 16. A user may use the monitoring device 26 during actuation of the actuator 20 to help ensure that the contrast media is being delivered at a particular rate and/or a substantially constant rate. The monitoring device 26 may comprise a dial or a digital display in various embodiments. The device 26 may be attached to the base 12. Although illustrated as attached to side 12s, the device 26 may be attached to another portion of the base. Similarly, although the crank 20 is shown attached to one end 12e of the base, it may be attached to another portion of the base, such as one of the sides 12s. Moreover, the base bottom 12b may be configured to be attached to a scanner or a gantry associated with a scanner.

The device 10 may provide several advantages. Such advantages may include: (1) ease of use compared to a single large syringe or several smaller interchangeable syringes; (2) increased throughput due to less time preparing for the injection; (3) increased patient safety since the operator can easily inject the contrast material and monitor the injection site simultaneously using finger palpation; (4) significant improvement in the quality of the CT scan due to markedly improved contrast enhancement profile; for example, this advantage could translate into improved detection of solid tumors in solid organs; (5) the potential for performing more CT protocols that require more demanding contrast material strategies, such as CT-angiography; (6) the ability to replace more costly electronic power injectors, particularly in practices that cannot afford expensive equipment, such as those in third world countries rural or underserved portions of the U.S.; and (7) for use as a back-up system, in the event of power failure.

Methods for assisting the hand-injection of contrast media during computer tomography are also contemplated. In one such operation, the device 10 is provided. The syringe 16 containing contrast media is positioned such that at least a portion of the syringe 16 (e.g., the syringe body 16b) is securely held by the compartment 14 and the syringe plunger 16p is received by the plate 18 in the first position P1. The actuator 20 is actuated to move the plate 18 and the syringe plunger 16p in the first direction D1. A constant injection rate of contrast media from the syringe is maintained.

In some embodiments, an intravenous (IV) line is established prior to actuating the actuator. This may be either a new or an existing IV line. It can be either a peripheral line (e.g., antecubital vein in the arm of a subject) or a central line (e.g., peripherally inserted central catheter (PICC) or central venous catheter). The syringe 16 may be removed from the device 10 filled with the desired contrast media. In some embodiments, the syringe 16 holds a volume of about 150 ml of contrast media, and is therefore compatible with all concentrations of iodine, even up to 400 mg/ml. This may be advantageous since the more concentrated agents have a higher viscosity and in some cases are virtually impossible to administer via a hand injection. For example, iopamidol 370 mg iodine/ml has only 23% more iodine but has a viscosity that is almost twice that of iopamidol 300 mg iodine/ml. Furthermore, the device 10 is also compatible with the pre-filled syringes which are currently available from the manufacturer (e.g., Bracco Diagnostics, Inc.). Syringes pre-filled with contrast material have the advantage of saving time but generally are a little more expensive.

The injection device 10 may be connected to the IV line with a high pressure tubing of appropriate length and the patient may be placed on a gantry of a scanner (i.e., when the patient is ready for acquisition) prior to actuating the actuator and delivering the contrast media.

In some embodiments, a constant pressure (PSI) or injection rate (ml/sec) of contrast media to the patient is established by monitoring the monitoring device 26.

Another potential advantage is the ease of use which allows the user performing the injection to simultaneously monitor the injection site using finger palpation with their other hand. Furthermore, in the event of a suspected contrast media extravasation or if the patient experiences the sudden onset of nausea and vomiting, the injection can be discontinued immediately by releasing the crank 20, for example.

Figure 2:
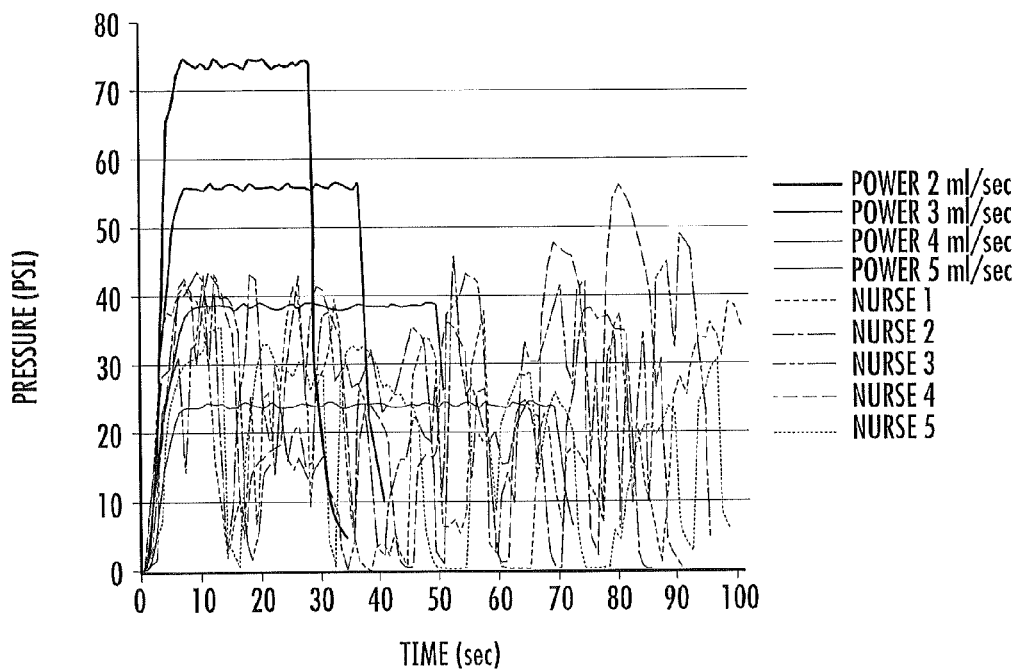
FIG. 2 is a graph illustrating a pressure injection profile over time comparing a power injector to hand-injection.

FIG. 2 depicts a pressure profile over time comparing injections using a power injector versus those administered by hand. Specifically, the graph shows a pressure profile over time during the power injection of 150 ml of iopamidol 300 mg iodine/ml at 2, 3, 4 and 5 ml/sec. Also shown are profile curves for five different administers (e.g., nurses) performing a hand injection using five different 30 ml syringes. Note the extreme variation in enhancement during a hand injection. Also note that during a hand injection there are intermittent pressures that exceed the pressure of a power injection at 2 ml/sec.

Figure 3:
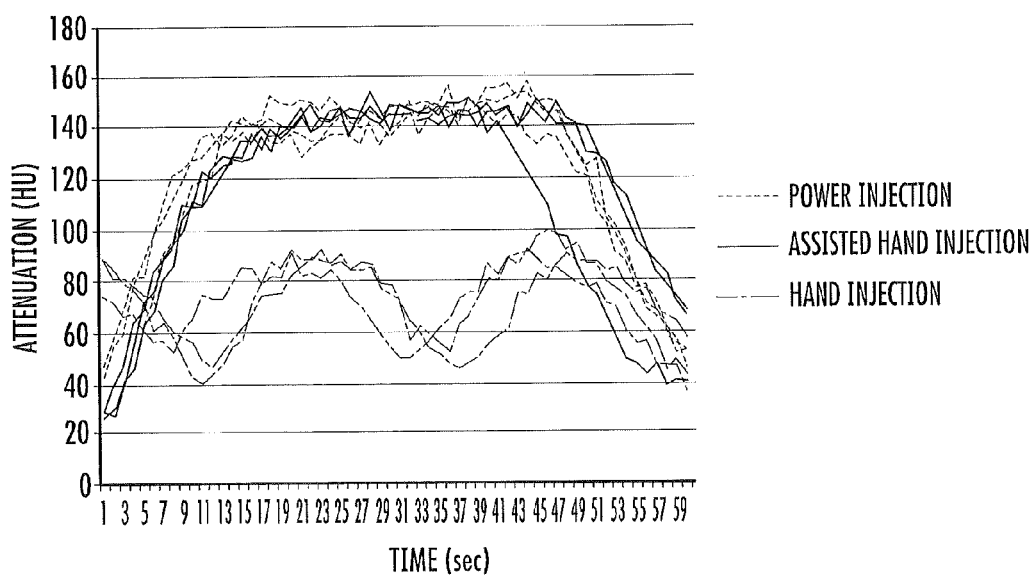
FIG. 3 is a graph illustrating a time attenuation curve comparing injections using a power injector, hand injections, and the device of FIG. 1.

In contrast, FIG. 3 shows a time attenuation curve comparing injections using a power injector, a device according to the present disclosure, and hand injection. Specifically, FIG. 3 shows time-attenuation curves for the injection of 150 ml of iopamidol 300 mg iodine/ml at 5 ml/sec. It can be seen that the power injection curve and the mechanically-assisted hand injection curve (i.e., using a device similar to the device 10) are very similar. The hand injection bend has much lower peak enhancement since five 30 ml syringes were used sequentially.

Turning now to FIGS. 4-12, intravenous catheters that deliver fluid into a peripheral vein while minimizing or eliminating a jet from a tip of the catheter are illustrated.

One potential advantage of a jetless catheter is that when it delivers fluid into the vein, whether iodinated contrast material, crystalloids (e.g., normal saline, 5% dextrose in water, lactated ringers, etc.) or blood products (e.g., whole blood, packed red blood cells, platelets, etc.), the potential for extravasation, whereby fluid is deposited outside the lumen of the vein into the surrounding soft tissue, is reduced. Such extravasation events can have severe deleterious effects on the patient, such as skin ulcerations and/or compartment syndrome. The most devastating severe adverse event is compartment syndrome, which is associated with a compromise in the blood supply to the hand, a neurologic deficit in the hand, or both. Severe reactions often require plastic surgery, either electively or urgently. If an ulcer develops, a skin graft is typically required on an elective basis to cover the soft tissue defect. If a compartment syndrome develops, one or more long incisions are required on an urgent basis to decompress the tissue. Even if the soft tissue damage is minor, a significant amount of time and effort is given to the patient by a physician and the nursing/support staff in order to prevent a serious injury (e.g., monitoring of pulses and sensation, elevation of the arm and application of cold compresses) and to document the event. In addition, in many cases the whole purpose of administering iodinated contrast material as a bolus is lost, thereby limiting the diagnostic capability of the scan. Not only is the bolus of contrast material disrupted but the timing is delayed, resulting in overall poor vascular and tissue enhancement.

Another potential advantage of a jetless catheter is that it may allow for the safe delivery of a higher volume of fluid in a shorter period of time. Higher flow rates may be advantageous in patients who have severe fluid depletion such as those in hemorrhagic shock following trauma. These patients can significantly benefit from rapid infusion of either crystalloids, blood products or both. In many patients who experience significant blood loss following major trauma, rapid fluid infusion may be the key to their survival. Another clinical scenario where a rapid intravenous infusion of a fluid substance is advantageous is with modern multi-detector row helical CT scanners. These scanners acquire a large number of images in a very short period of time (e.g., the entire abdomen and pelvis in 5 seconds or less), and are optimized from a diagnostic standpoint when performed following the administration of intravenous iodinated contrast material. To take advantage of the speed of the scanners, a bolus of contrast material must be rapidly administered into a vein, typically located in the arm. This results in a short but vivid period of vascular and tissue enhancement and thereby improves the detection of pathologic processes. Matching scanner speed with rapid contrast media administration may improve the efficacy of contrast-enhanced CT in a wide variety of clinical applications. For example, the detection of highly vascular lesions in the liver or pancreas may be improved by administering the contrast media at a high rate during a CT scan. Also, the use of highly concentrated iodinated contrast material (e.g., 370 mg of iodine/ml vs. 300 mg of iodine/ml) may further improve this enhancement profile, particularly during the arterial phase. Contrast media with higher concentrations of iodine, however, are much more viscous, making them thick and difficult to inject intravenously. A jetless catheter according to some embodiments can allow for the very rapid and safe infusion of even the most viscous iodinated contrast agents in CT and/or obviate the need for larger caliber angiocaths. Larger caliber angiocaths are not only more difficult to insert and establish, but are also more painful to the patients.

Figure 4:
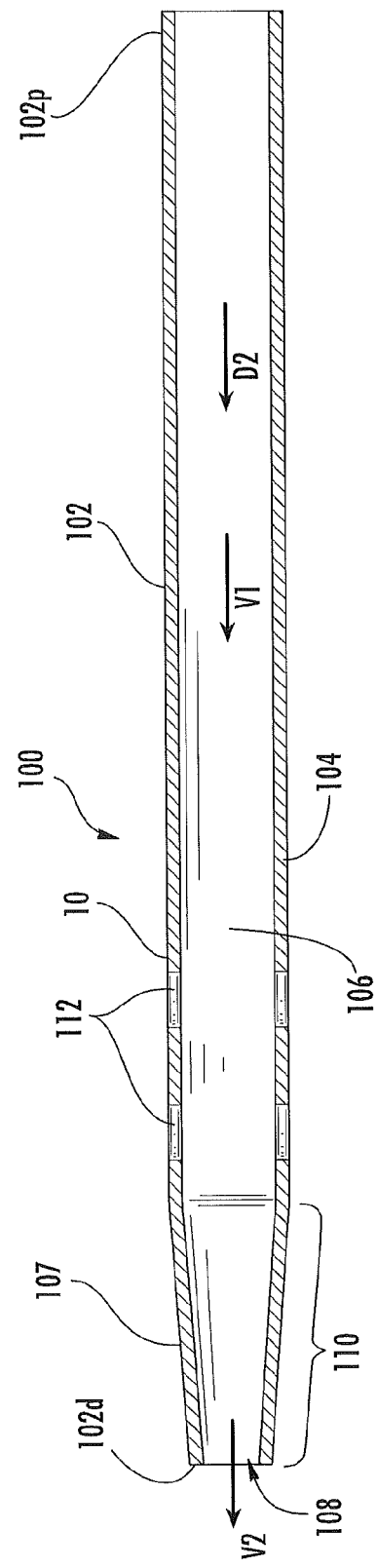
FIG. 4 is a side cross-section view of a jetless catheter including at least one flow reducing feature according to some embodiments.

Referring now to FIG. 4, a jetless intravenous catheter 100 is illustrated. The catheter 100 has an elongated body 102 having opposite proximal and distal ends 102*p*, 102*d*. The body 102 includes a wall 104 defining an internal fluid passageway 106 through which fluid may flow in a longitudinal direction D2 from the proximal end 102*p* toward the distal end 102*d* of the body 102. A tip 107 defines an aperture 108 located at the body distal end 102*d*; fluid flowing through the passageway 106 may exit the body 102 through the tip aperture 108. As illustrated, the body 102 may include a tapered section 110 extending from the distal end 102*d*. The tip 107 forms at least part of the tapered section 110.

In some embodiments, the body 102 is constructed of a polymeric material such as Teflon™. In some embodiments, the wall 104 has a thickness of about 100 μm, although the wall may be thinner or thicker in other embodiments. The catheter 100 may be any suitable size including, but not limited to, calibers of 18, 20 and 22 gauge. These calibers correspond to an internal diameter of 870, 690 and 540 μm, respectively. The catheter length (i.e., the length of the body 102 from the proximal end 102*p* to the distal end 102*d*) may be between about 2 cm to about 6 cm, and, in some embodiments, may be between about 3 cm to about 5 cm. Although these sizes and lengths match angiocaths that are currently available, smaller caliber catheters are easier to insert into the patients and are preferred by nursing staffs. Hence, such catheters are within the scope of the present disclosure.

The body 102 includes at least one flow reducing feature configured to reduce the flow velocity of fluid exiting the tip aperture. For example, the flow reducing feature may be at least one aperture 112 in the wall 104 (as illustrated, the flow reducing feature is a plurality of wall apertures 112). As shown in FIG. 4, fluid can flow in the longitudinal direction D2 at a first axial velocity V1 upstream of the wall apertures 112, and the fluid can exit the tip aperture 108 (i.e., downstream the wall apertures 112) at a second axial velocity V2 that is less than the first axial velocity V1.

Figure 5:
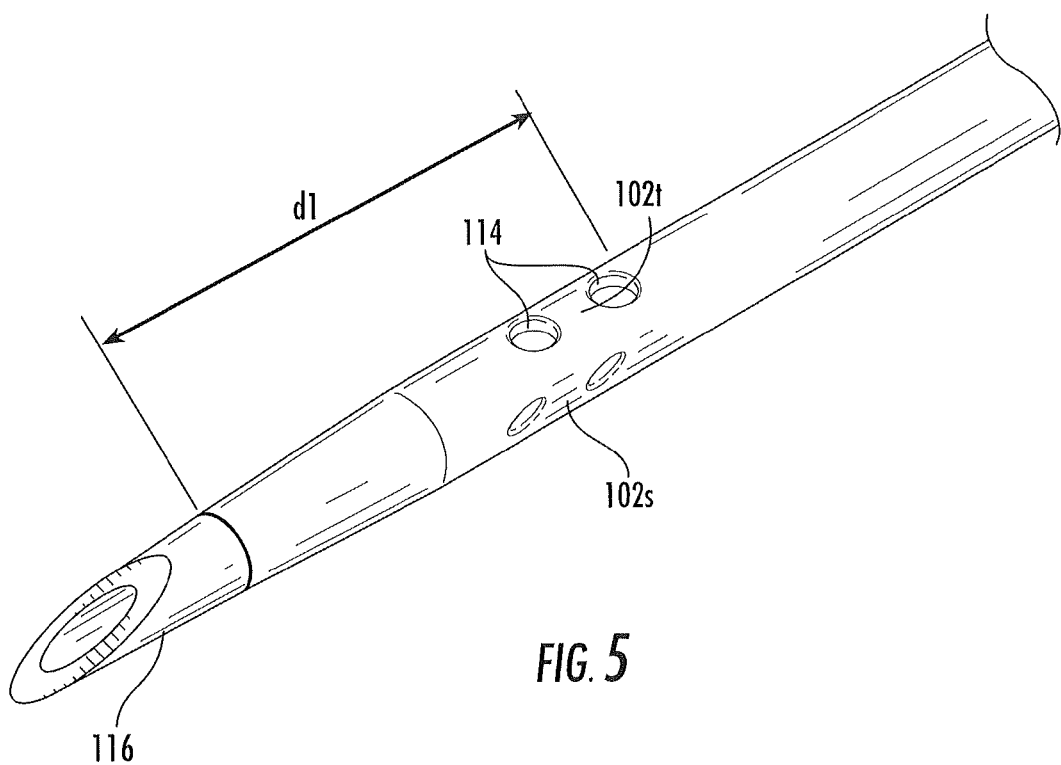
FIG. 5 is a perspective view of a portion of the jetless catheter according to some embodiments having a stylet therethrough wherein the flow reducing feature comprises holes.

Referring to FIG. 5, the catheter 100 is shown having a stylet 116 inserted therethrough. The stylet 116 may be inserted through the passageway 106 of the catheter body 102. The stylet 116 is constructed of a rigid material (e.g., stainless steel) to provide stiffness to the catheter 100 as it is being inserted into a vein of a subject. In some embodiments, and as illustrated, the stylet 116 is hollow to allow for the back filling or back flash of blood which indicates that the distal end 102d of the catheter body 102 is in the lumen of the vein. Also as illustrated, a tip 118 of the stylet 116 is slant-cut (i.e., beveled) and sharp to facilitate easy piercing of both the skin and the most superficial wall of the vein. The stylet 116 has a length such that the stylet 116 extends about 2 mm beyond the distal end 102d of the catheter body 102.

Turning back to FIG. 4, the wall apertures 112 may be clustered relatively close to the distal end 102d of the body 102 to ensure that all the wall apertures 112 are located in a vessel lumen after insertion into a subject. The position, shape, and size of the apertures 112 is selected with this in mind, while also maintaining the structural integrity of the catheter body 102. Therefore, in various embodiments, the wall apertures 112 are positioned from about 1 mm to about 12 mm, from about 2 mm to about 11 mm, or from about 3 mm to about 10 mm from the distal end 102d of the body 102. As will be described below, the wall apertures 112 may be round holes or may be slits, and may be sized, shaped and positioned so as to not substantially weaken the tensile properties of the body 102.

The catheters in accordance with the present disclosure are for use in intravenous injection of fluids at high injection rates. As described above catheters incorporate a plurality of apertures or openings on the catheter wall to allow some portion of the fluid to escape from the catheters wall, thus reducing the amount and, therefore, flow speed of fluid exiting the catheter tip. With the reduced catheter tip flow speed, injections will be less likely to damage the endothelial wall on the inside of the artery or vein. In addition, the reduced speed of the tip jet will reduce the likelihood of a patient experiencing an extravasation event.

The design of the catheter body 102 allows for the simultaneous exit of fluid or blood products through a plurality of different apertures in a distal portion of the body 102. For the flow conditions present in vivo, the fluid exit pressure (whether from the tip aperture 108 or the wall aperture 112) will be identical to the pressure in the vessel. The exit velocity depends on the difference in pressure between the interior and exterior of the catheter wall 104 and on the viscous forces opposing the flow. Each wall aperture 112 is typically smaller than the tip aperture 108, and the viscous forces will be greater for the wall aperture 112 than for the tip aperture 108. Therefore, the fluid exit velocity for a relatively small wall aperture 112 will be less than the exit velocity V2 from the catheter tip aperture 108. Additionally, as some fraction of the flow exits from the wall apertures 112, the pressure between the interior and exterior of the catheter wall 104 will decrease toward the more distal region of the tip. Because the tip pressure difference is less for the presently disclosed catheter design than for a conventional catheter without wall apertures, the tip jet will be reduced in strength. The reduction in tip jet strength or velocity exiting the tip aperture 108 can result in fewer clinical instances of extravasation.

The aperture(s) 112 may take the form of at least one substantially circular hole 114 or, as illustrated in FIG. 5, a plurality of substantially circular spaced-apart holes 114. There may be at least one hole 114 on one or both of diametrically opposed sides 102s. A through-and-through hole in the wall 104 may form these diametrically opposed holes 114 (or any other diametrically opposed apertures disclosed herein) or any diametrically opposed hole 114 may be formed individually (likewise for any diametrically opposed aperture disclosed herein). Alternatively or additionally, there may be at least one hole 114 on a top 102t of the body 102 and at least one hole 114 on a bottom of the body 102 (not visible) that is diametrically opposed from the body top 102t. In some embodiments, the top 102t of the body 102 includes holes 114 but no holes are formed in the diametrically opposed bottom of the body. This configuration may be advantageous because the bottom of the body 102 may be adjacent a vessel wall when the body 102 is inserted therein and fluid flowing from one or more holes on the bottom of the body 102 may therefore impinge on the vessel wall.

As used herein, the terms "top," "side," and "bottom" used in reference to the catheter body 102 are defined as shown in the figures, and is also with reference to the tabs typically found on catheter hubs.

In some embodiments, there may be a longitudinally-arranged row of spaced-apart holes 114 on one or both of the diametrically opposed sides 102s of the body 102. In some embodiments, and as illustrated, there may be a longitudinally-arranged row of spaced-apart holes 114 on the top 102t of the body 102. At least some of the rows of holes 114 may be staggered with respect to one another. For example, the row of holes 114 on the top 102t of the body 102 may be staggered with respect to the row of holes 114 on the side 102s of the body 102. In other words, the hole 114 on the body top 102t closest to the body distal end 102d or tip 107 may be closer to the distal end 102d or tip 107 than the hole 114 on the body side 102s closest to the body distal end 102d or tip 107. In some embodiments, the hole 114 furthest from the distal end 102d or tip 107 may be located a distance d1 that is less than about 12 mm and, in some embodiments, less than about 10 mm, to help ensure that no holes 114 are positioned outside the vessel lumen after the catheter body 102 has been inserted therein.

Figure 6:
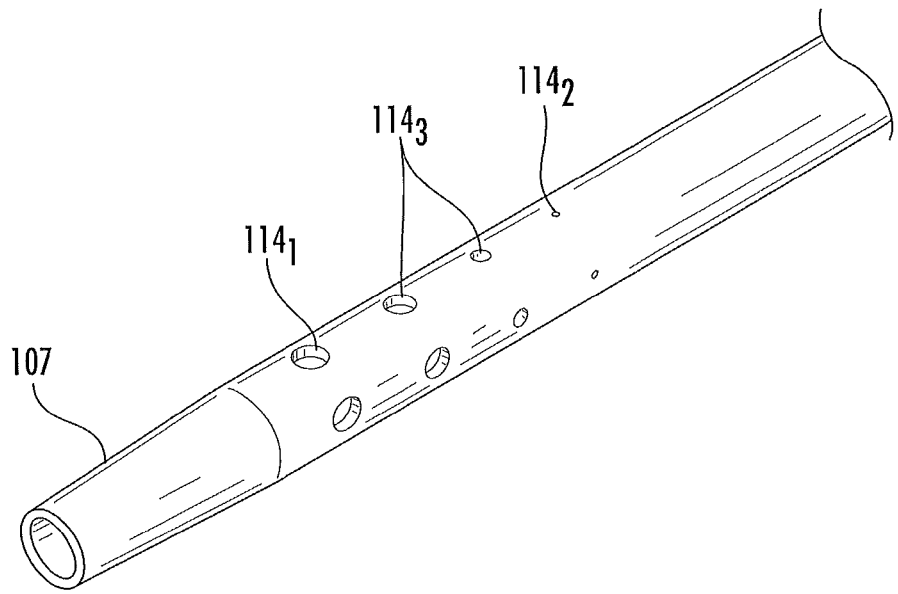
FIG. 6 is a perspective view of a portion of the jetless catheter according to some embodiments wherein the flow reducing feature comprises holes.

Turning to FIG. 6, in some embodiments, holes 114 of varying diameter can make up a particular row of holes. As illustrated, a first hole $114_1$ closest to the body distal end 102d or tip 107 has a first diameter and a second hole $114_2$ furthest from the distal end 102d or tip 107 has a second diameter that is less than the first diameter. At least one third hole $114_3$ is positioned between the first and second holes $114_1$, $114_2$ and has a third diameter that is between the first and second diameters. In this configuration, a reduced diameter hole 114 furthest from the distal end 102d or tip 107 may reduce the likelihood that the hole will be positioned outside the vessel lumen after insertion into a vessel. Furthermore, it is contemplated that the hole $114_3$ at the body top 102t can be positioned closer to the distal end 102d or tip 107 than corresponding holes on the diametrically opposed sides 102s. This may be accomplished, for example, by staggering the holes in each respective row and/or by include fewer holes in the row on the body top 102t. This may be advantageous because the catheter tip 107 is often directed obliquely or at an angle to the vessel wall, with the result that the body top 102*t* does not extend as far into the vessel lumen as the body sides 102*s*. It is also contemplated that the at least some of the holes in a particular row could have decreasing diameter as they approach the body distal end 102*d* or tip 107 in the longitudinal direction (e.g., the reverse configuration than that shown in FIG. 6).

In some embodiments, at least some of the holes 114 are at least about 75 µm in diameter, and, in some embodiments, at least about 100 µm in diameter, to accommodate both crystalloids and blood products (red blood cells are about 7 µm, white blood cells are about 20 µm). The various holes 114 could all be the same diameter (e.g., uniform holes), or at least some of the holes 114 could have different diameters.

Figure 7A:
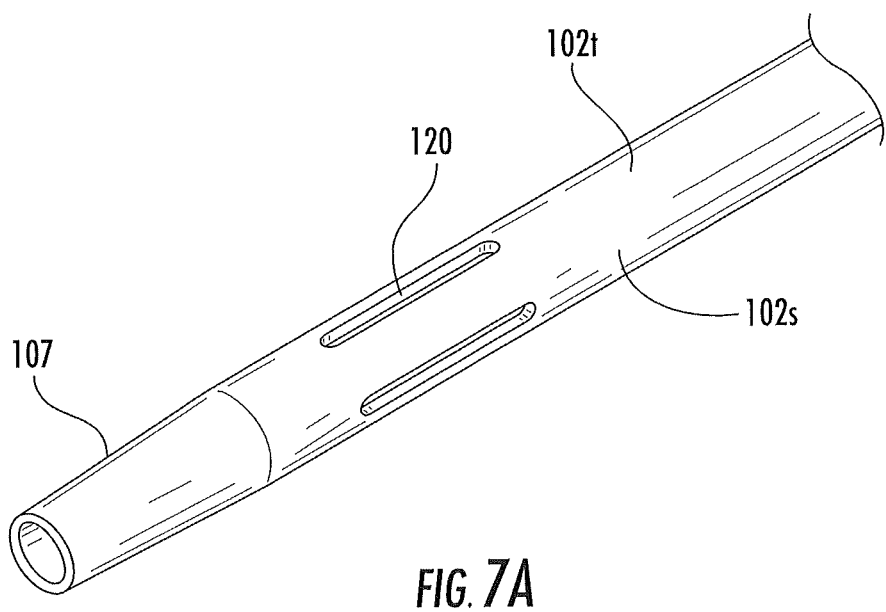
FIG. 7A is a perspective view of a portion of the jetless catheter according to some embodiments wherein the flow reducing feature comprises uniform slits.

Turning now to FIG. 7A, in some embodiments, the wall apertures comprise longitudinally-extending slits 120. As illustrated, a plurality of slits 120 may be provided with a slit 120 on one or both of the diametrically opposed sides 102*s* and/or a slit 120 on the top 102*t*. A slit 120 may also be included on a bottom of the body 102 (not visible) that is diametrically opposed from the top 102*t*. In some embodiments, the bottom of the body 102 does not include a slit as this surface may reside adjacent a vessel wall after insertion of the catheter and fluid flowing therefrom could impinge on the wall.

In various embodiments, the slits may extend from about 4 mm to about 12 mm from the body distal end 102*d*, from about 4 mm to about 10 mm from the distal end 102*d*, from about 5 to about 10 mm from the distal end 102*d*, or from about 6 mm to about 10 mm from the distal end 102*d*. In some embodiments, the slits 120 have a length of less than 5 mm and extend no further than 10 mm from the distal end 102*d* of the body 102. Terminating the slits 120 at less than about 12 mm or less than about 10 mm from the distal end can help ensure that the slits are located within a vessel lumen after the catheter has been inserted therein. In various embodiments, the slits have a width of less than 100 µm, less than 50 µm, and less than 25 µm.

Figure 7B:
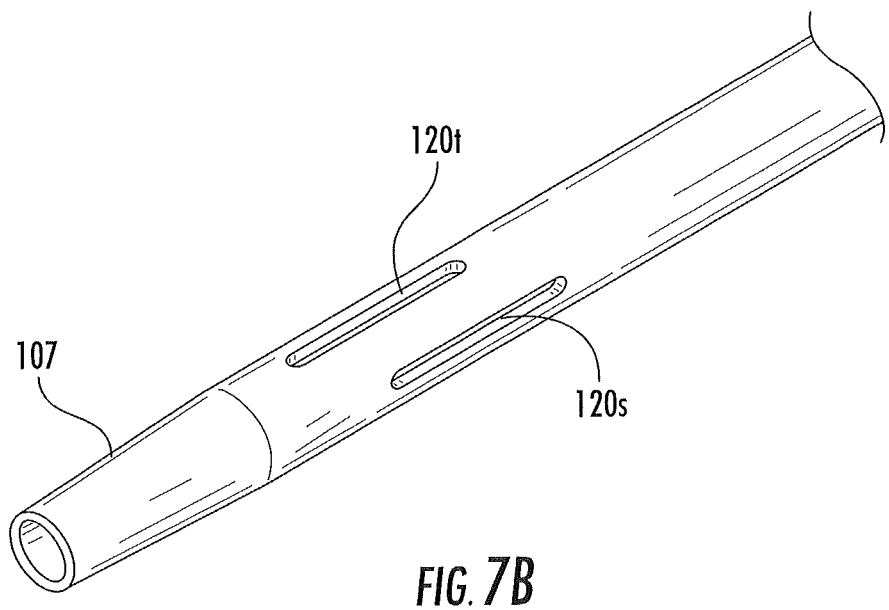
FIG. 7B is a perspective view of a portion of the jetless catheter according to some embodiments wherein the flow reducing feature comprises staggered uniform slits.

Turning to FIG. 7B, a slit 120*t* located on the body top 102*t* can be staggered relative to slits 120*s* located on the diametrically opposed body sides 120*s*. In this regard, the slit 120*t* terminates at a point that is closer the distal end 102*d* or tip 107 than the slits 120*s*. Again, catheters are often inserted at an angle to the vessel wall such that the top 102*t* does not extend as far into the vessel lumen as the diametrically opposed sides 102*s*. Thus, this configuration helps ensure that the slit 120*t* associated with the top 102*t* does not extend outside the vessel lumen. This potential advantage can also be realized by providing a slit on the top 102*t* that is not as long as those on the diametrically opposed sides 102*s* such that the slit on the top 102*t* terminates a lesser distance from the distal end of the body 102*d* or tip 107. Other staggered slit configurations are contemplated; for example, a slit on the top 102*t* could terminate at a point that is further from the distal end 102*d* or tip 107 than the slits on the sides 102*s*.

Figure 8:
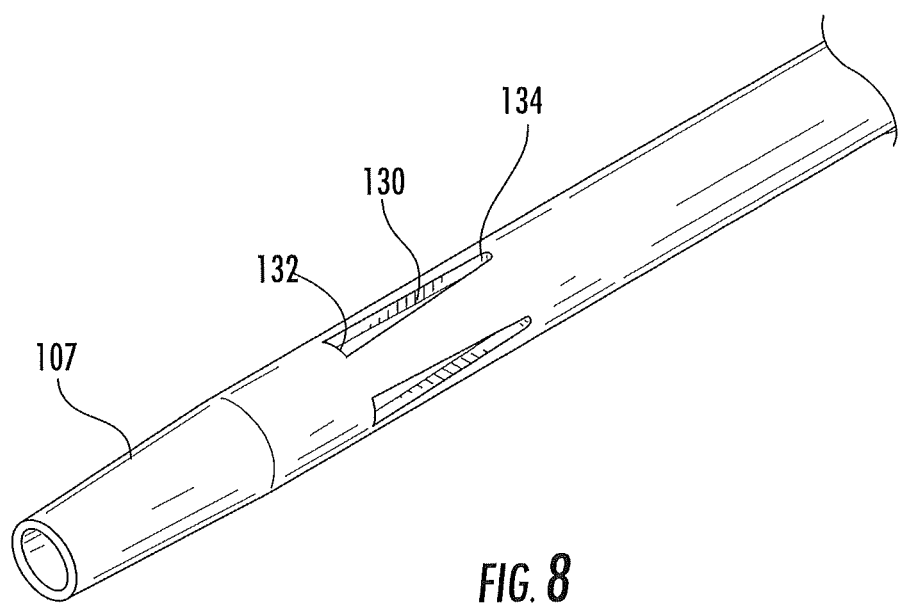
FIG. 8 is a perspective view of a portion of the jetless catheter according to some embodiments wherein the flow reducing feature comprises tapered slits.

Referring now to FIG. 8, tapered slits may be provided. In this regard, a slit 130 can have a first end 132 closest to the distal end 102*d* that is wider than a second end 134 furthest from the distal end 102*d* or tip 107. The slits may also widen as they extend away from the distal end 102*d* or tip 107 (i.e., the reverse configuration from that shown in FIG. 8). It is contemplated that the embodiments shown in FIGS. 7B and 8 can be combined; that is, the flow reducing feature could comprise tapered slots that are staggered with respect to one another The presence of wall apertures may reduce the volumetric flow from the catheter tip aperture. In some embodiments, the spacing between the wall apertures and the shape of the wall apertures are such that the disturbance created by these apertures on the flow within center of the catheter (i.e., fluid flowing in the longitudinal direction through the passageway 106 from the proximal end 102*p* as shown in FIG. 4) will create a laminar-to-turbulent transition and/or destabilize the flow. The destabilized axial flow can more readily overcome the large momentum of the high velocity catheter flow and therefore more readily exit the wall apertures. In addition, the destabilized flow may mix more easily once it leaves the catheter. Without being bound by theory, in some embodiments, the wall apertures are configured to excite the Tollmien-Schlichting instability associated with the fluid flowing through the passageway 106.

Catheters with longitudinal slits or openings in the sidewalls have been described, for example, in U.S. Pat. No. 5,250,034 to Appling et al. and U.S. Pat. No. 5,857,464 to Desai, the disclosures of which are incorporated herein in their entireties. However, the slits or openings are not arranged so as to create a laminar-to-turbulent transition.

In contrast, the catheters described herein include features (e.g., wall apertures) arranged to destabilize the fluid. For example, the features may create a laminar-to-turbulent transitional flow instability, create a Reynolds instability, excite the Tollmien-Schlichting instability associated with the fluid, and/or create any other flow instability. As a result, the maximum velocity occurs inside the catheter itself, and more particularly upstream of the wall apertures, as opposed to occurring at the tip aperture. This is shown schematically in FIG. 4, with the upstream velocity V1 being greater than the downstream velocity V2. Accordingly, the maximum fluid velocity is not impinging on the vessel wall. Indeed, the addition of side holes and side slits to standard angiocatheters in the configurations described herein experimentally resulted in a plume rather than a jet of contrast material exiting the catheter tip.

Furthermore, standard catheters direct all of the shear stress onto the wall region adjacent to the tip, whereas the catheters with wall apertures arranged in the manner disclosed herein spread out the higher shear stress regions, with the fluid flowing from the wall apertures producing smaller, localized shear stress regions. In other words, the higher shear stress region produced by the tip is diminished by the disclosed configurations of the wall apertures which create instability such that the high momentum axial flow can be overcome and permit a portion of the fluid to exit the wall apertures. This may be especially true where high flow rates and/or highly viscous fluids are employed, such as with contrast media used in modern computer tomography techniques.

In some embodiments, catheters for use in the injection of fluids with tip shapes that disperse the fluid exit jet are provided. Again, when fluids are injected into patients at high rates, such as during the administration of contrast enhancing media for CT or MR imaging studies, the fluids can exit the catheter tip at high velocities. There is a possibility that the fluid leaving the tip at a high velocity could impinge upon the interior vessel wall and cause injury or extravasation. In accordance with some embodiments, and as shown in FIG. 9, catheters with non-axis symmetric tip geometries may be designed to rapidly disperse the jet once the fluid exits the catheter tip.

Figure 9:
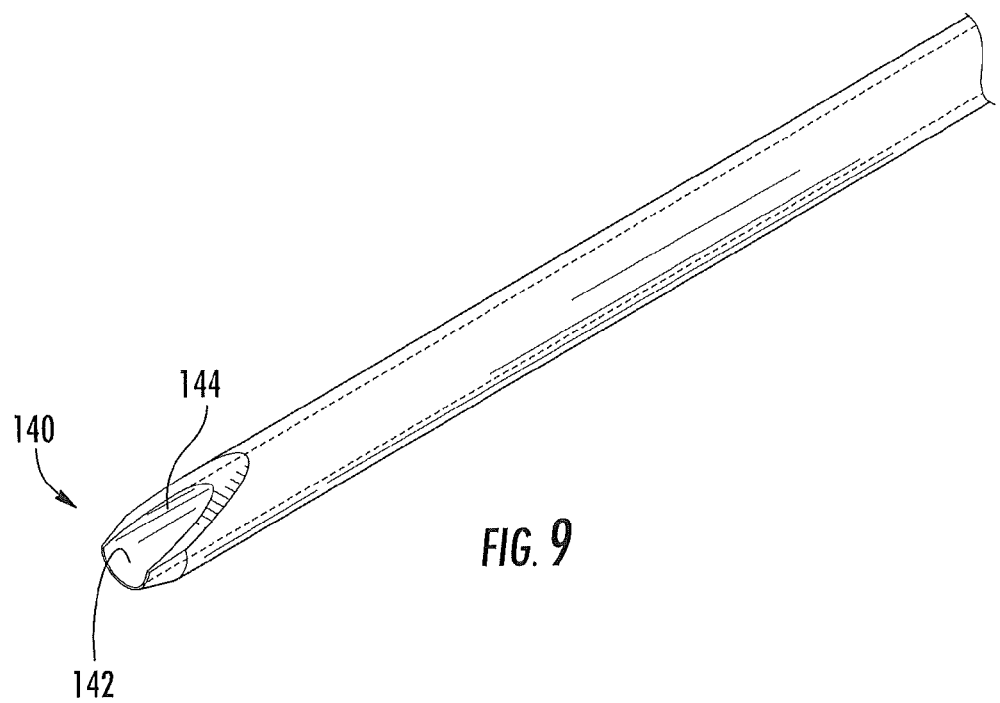
FIG. 9 is a perspective of a portion of a catheter including a beveled tip according to some embodiments.

The tip 140 illustrated in FIG. 9 is beveled such that flow of a fluid therethrough is dispersed between a closed bottom portion 142 and an inwardly and upwardly extending open portion 144. Once a catheter has been inserted past a first vessel wall, the catheter tip is often adjacent the opposite wall inside the vessel lumen. The configuration of the tip 142 may reduce impingement and shear stress against the adjacent vessel wall because the flow is urged upward away from the wall and is more readily dispersed. It is contemplated that the tip configuration shown in FIG. 9 may be advantageously combined with the flow reducing features described herein to further minimize impingement against a vessel wall and to further reduce shear stress at the wall.

Figure 10:
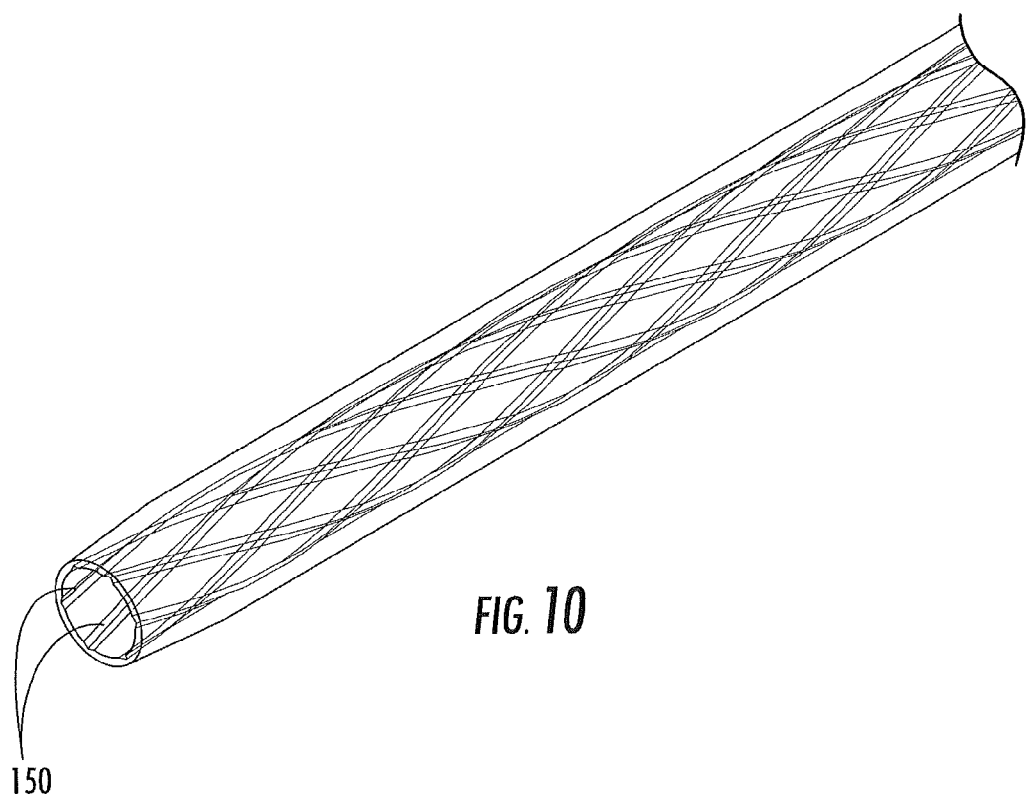
FIG. 10 is a perspective view of a portion of a catheter including internal spiral grooves according to some embodiments.

In some embodiments, and as shown in FIG. 10, a catheter comprises internal spiral grooves 150. The grooves 150 may be formed in an interior of the wall and may be helically disposed in the longitudinal direction. The internal grooves 150 are configured to create a vortical flow in the injected medium. This vortical flow causes the medium to disperse rapidly once it exits the tip of the catheter. Since the medium disperses rapidly after leaving the catheter tip, it may cause less vessel wall damage or lessen the possibility of extravasation. It is contemplated that the spiral grooves 150 could be advantageously employed with other embodiments described herein. For example, the spiral grooves 150 could be employed upstream and/or downstream of the flow reducing features described above to further encourage the laminar-to-turbulent transition flow and encourage fluid flow out of the wall apertures and/or to encourage fluid dispersion at the tip.

Figure 11:
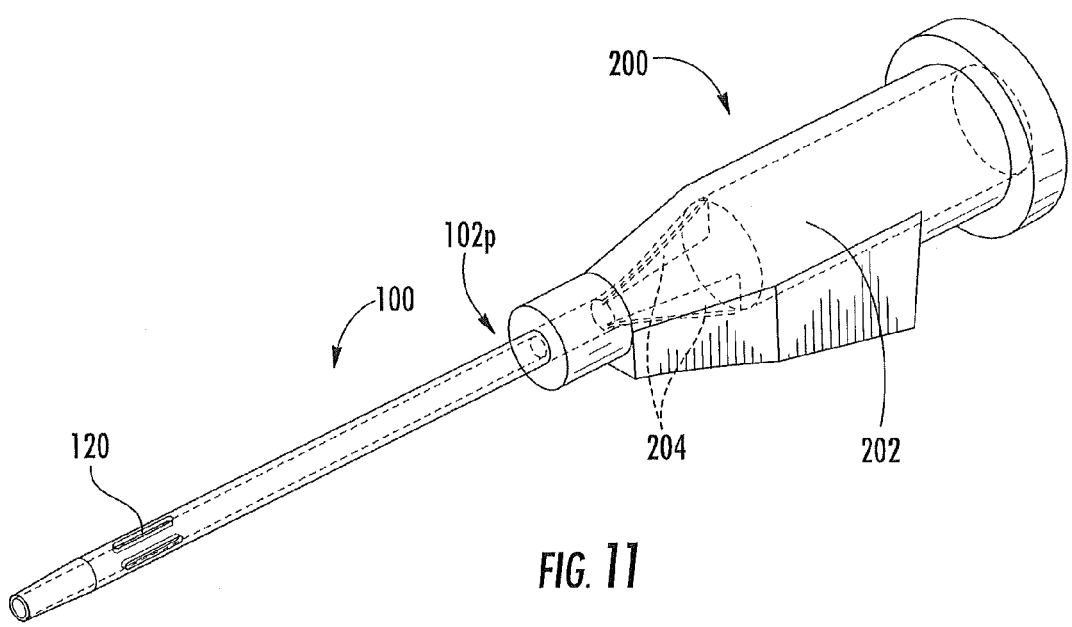
FIG. 11 is a perspective view of a catheter hub connected to the catheter of FIG. 7A.
Figure 12:
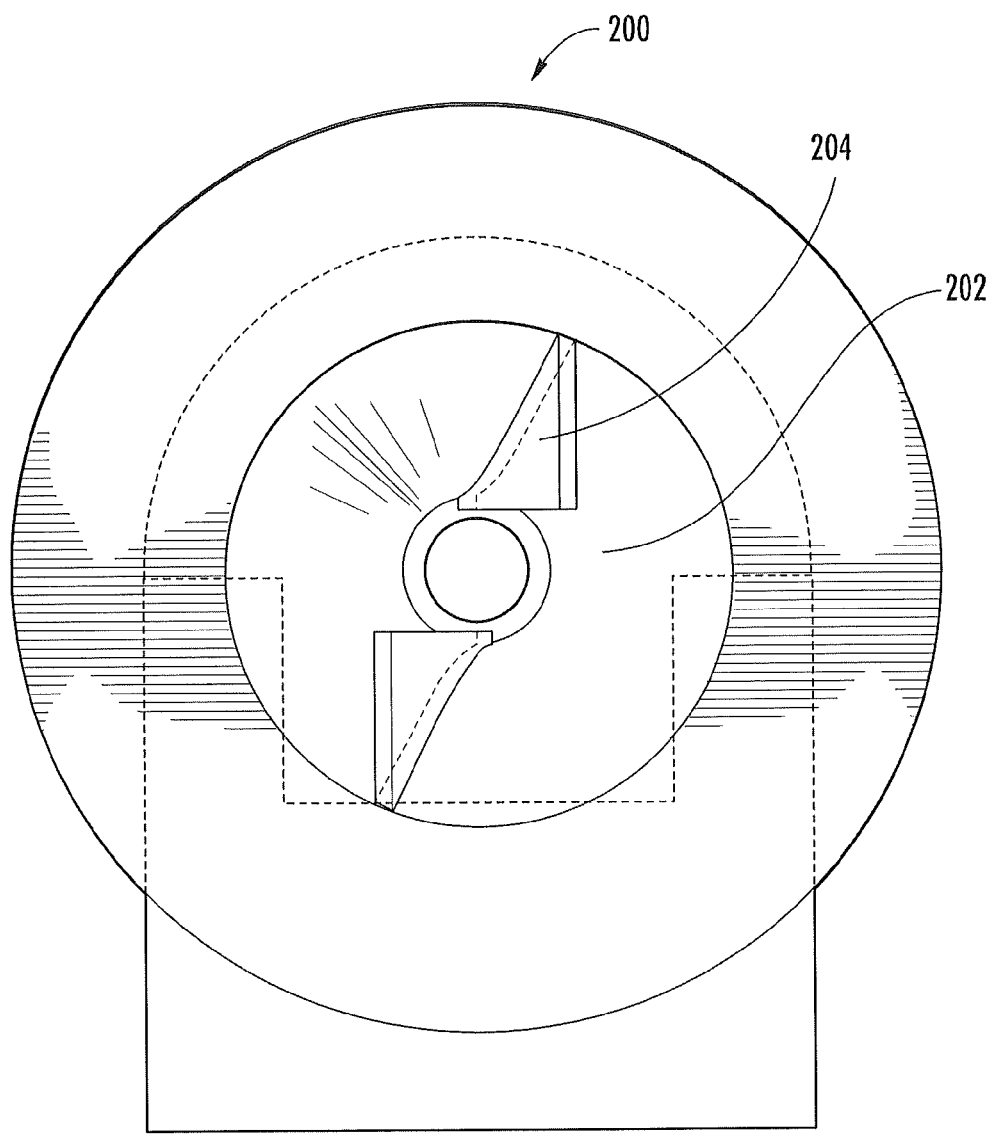
FIG. 12 is a rear view of the catheter hub and catheter of FIG. 11.

Referring now to FIGS. 11 and 12, a catheter hub 200 is connectable to the catheter body proximal end 102p. The hub 200 has an interior cavity 202 through which fluid may flow into the catheter body at the proximal end 102p. The interior cavity 202 includes at least one vorticity introducing feature therein that is configured to introduce vorticity to fluid flowing through the interior cavity 202 and into the catheter body. The vorticity introducing feature can comprise at least one groove or at least one fin, for example. As illustrated, the vorticity introducing feature comprises a plurality of fins 204 designed to introduce vorticity to the flow of the fluid through the catheter of the body. In certain embodiments, the hub 200 accompanies previous catheter designs described herein containing different arrangements of holes and slits near the tip of the catheter. For example, as illustrated in FIG. 11, the hub 200 can be used in combination with a catheter 100 including a plurality of longitudinally-extending slits 120. However, any suitable catheter, including the catheters illustrated in FIGS. 4-10, may also be used. The vorticity increases the amount of fluid that escapes from the side holes and slits, further reducing the stress applied to the blood vessel and decreasing the likelihood of an extravasation event.

In some embodiments, the fins 204 vibrate to cause a disturbance in the flow. In such embodiments, the fins 204 may have geometrical and material properties such that their resonant frequency is matched by the desired flow rate. The hub 200 can be used in combination with any suitable catheter, including one of the previous catheter designs described herein with an arrangement of holes and slits in the catheter body, thereby increasing the amount of fluid that exits the catheter through the side holes and slits.

Another aspect of the present disclosure provides a method for high-frequency (e.g., greater than 1 Hz) periodic modulation of injection pressure and flow rate. The high-frequency modulation is designed to destabilize the flow of the injected medium by encouraging laminar-to-turbulent flow. The high-frequency modulations may take place either due to mechanical or acoustic forcing at the mechanical injector or at any point in the flow circuit external to the patient. In some embodiments, this modulation is paired with flow circuit hardware specifically tuned to resonate at the driving frequency. This may further enhance instability in the flow and cause the medium to disperse more quickly once it exits the catheter tip.

Notably, the catheters in some embodiments do not contain any flaps to vibrate or dislodge, and the catheters do not change shape following insertion as a result of heat or during the injection of fluid as a result of pressure or fluid shearing force. Moreover, in some embodiments, the removal of the stylet after intravenous access reveals the end hole as well as the multiple wall apertures that are positioned such that the catheter will only need to enter the vein a total of about 10 mm to ensure that all of the side holes are within the lumen.

Also within the scope of the present disclosure is a laser machining process for creating the wall apertures in intravenous catheters. A laser machining process for beveling catheter tips is described in U.S. Pat. No. 5,425,803 to van Schravendijk et al. However, the laser machining process according to the present disclosure involves the creation of a plurality of wall apertures in catheter walls with a geometric arrangement such at that the openings encourage destabilized flow and/or create laminar-to-turbulent transitional flow.

According to some embodiments of the present invention, an assembly for assisting the rapid hand injection of contrast media into a peripheral vein of a subject and minimizing a jet of contrast media into the peripheral vein during computer tomography is provided. In some embodiments, the assembly includes the mechanically-assisted hand injection device 10 depicted in FIG. 1 and also includes one of the catheters described in the present application. A syringe (16, FIG. 1) may also be included, with the syringe tip 16t in communication with the catheter. High-pressure tubing may be used to connect the syringe tip 16t to the catheter.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A jetless intravenous catheter for the delivery of a fluid, comprising:
an elongated body having proximal and distal ends, the body including a wall defining an internal fluid passageway configured to receive fluid flowing in a longitudinal direction from the proximal end at a first axial velocity and a tip aperture at the distal end configured to allow fluid to exit therethrough, the body including a constant diameter section and a tapered section extending from the distal end to the constant diameter section;
wherein the body comprises at least one flow reducing feature configured to create a laminar-turbulent transitional flow associated with a fluid flowing in the constant diameter section in the longitudinal direction at the first axial velocity and configured to reduce the flow velocity of fluid exiting the tip to a second axial velocity that is less than the first axial velocity;
wherein the at least one flow reducing feature comprises a plurality of apertures in the wall of the constant diameter section such that a portion of a fluid flowing in the longitudinal direction exits the body through the plurality of apertures;

wherein the wall of the constant diameter section comprises a top surface and a diametrically opposed bottom surface and first and second diametrically opposed side surfaces that are each disposed between the top surface and the bottom surface, wherein each of the top, bottom and first and second side surfaces have the same arc length along the constant diameter section, and wherein each of the top, bottom and first and second side surfaces extends along an entire longitudinal length of the constant diameter section; and wherein the plurality of apertures comprises at least one aperture in the top surface of the wall of the constant diameter section and at least one aperture in each of the first and second side surfaces of the wall of the constant diameter section, and wherein the bottom surface of the wall of the constant diameter section does not include an aperture.

2. The jetless intravenous catheter of claim 1, wherein the plurality of apertures comprises a plurality of substantially circular spaced-apart holes.

3. The jetless intravenous catheter of claim 2, wherein the plurality of holes comprises a first row of spaced-apart holes aligned in the longitudinal direction in the first side surface of the wall of the constant diameter section and a second row of spaced-apart holes aligned in the longitudinal direction in the second side surface of the wall of the constant diameter section.

4. The jetless intravenous catheter of claim 3, wherein the plurality of holes comprises a third row of spaced-apart holes aligned in the longitudinal direction in the top surface of the wall of the constant diameter section.

5. The jetless intravenous catheter of claim 4, wherein the third row of holes includes a first hole closest to the distal end that has a first diameter, a second hole furthest from the distal end that has a second diameter that is greater than or less than the first diameter, and a third hole positioned between the first and second holes that has a third diameter that is between the first and second diameters.

6. The jetless intravenous catheter of claim 1, wherein the plurality of apertures comprises a plurality of elongated slits extending in the longitudinal direction.

7. The jetless intravenous catheter of claim 6, wherein the plurality of slits includes at least one slit in the top surface of the wall of the constant diameter section and at least one slit in each of the first and second side surfaces of the wall of the constant diameter section.

8. The jetless intravenous catheter of claim 7, wherein the plurality of slits are staggered such that the slit in the top surface of the wall of the constant diameter section extends closer to the distal end of the body than the slits in the first and second side surfaces of the wall of the constant diameter section.

9. The jetless intravenous catheter of claim 6, wherein each slit is tapered in the longitudinal direction such that the slit narrows or widens as the slit extends away from the distal end of the body.

10. The jetless intravenous catheter of claim 1, wherein the flow reducing feature is configured to excite the laminar-turbulent transition instability associated with a fluid flowing in the constant diameter section in the longitudinal direction.

11. The jetless intravenous catheter of claim 1, further comprising a hub connectable to the proximal end of the body, the hub having an interior cavity with at least one vorticity introducing feature configured to introduce vorticity to fluid flowing therethrough and into the fluid passageway of the body.

12. The jetless intravenous catheter of claim 11, wherein the at least one vorticity introducing feature of the hub comprises at least one of at least one groove, at least one fin, and at least one vibrating fin.

13. The jetless intravenous catheter of claim 11, wherein the at least one vorticity introducing feature of the hub comprises at least one groove in the hub.

14. The jetless intravenous catheter of claim 11, wherein the at least one vorticity introducing feature of the hub comprises at least one fin in the hub.

15. The jetless intravenous catheter of claim 14, wherein the at least one fin comprises at least one vibrating fin in the hub.

16. The jetless intravenous catheter of claim 1, further comprising a stylet positioned within the internal fluid passageway, the stylet having a beveled distal end that extends past the distal end of the body.

17. The jetless intravenous catheter of claim 1, wherein the at least one flow reducing feature is configured to excite the Tollmien-Schlichting instability associated with a fluid flowing in the constant diameter section in the longitudinal direction at the first axial velocity.

18. The jetless intravenous catheter of claim 1, wherein at least one groove is formed in an interior of the wall, with the at least one groove helically disposed in the wall along the longitudinal direction including in the wall of the constant diameter section.

19. An intravenous catheter for the delivery of a fluid, comprising:

an elongated body having proximal and distal ends, the body including a wall defining an internal fluid passageway configured to receive fluid flowing in a longitudinal direction from the proximal end and a tip including an aperture at the distal end configured to allow fluid to exit therethrough;

wherein the body comprises at least one fluid dispersing feature configured to disperse a fluid jet associated with a fluid flowing in the longitudinal direction as the fluid exits the tip aperture, and wherein the fluid dispersing feature comprises a partially beveled open top portion of the tip that extends to the distal end of the body and which is diametrically opposed to a closed bottom portion of the tip.

20. The intravenous catheter of claim 19, wherein the body surrounding the partially beveled open top portion of the tip and the distal end of the body at the closed bottom portion of the tip define the aperture.

21. The jetless intravenous catheter of claim 19, wherein:

the body includes a constant diameter section and a tapered section extending from the distal end to the constant diameter section;

the body comprises at least one flow reducing feature configured to create a laminar-turbulent transitional flow associated with a fluid flowing in the constant diameter section in the longitudinal direction at a first axial velocity and configured to reduce the flow velocity of fluid exiting the tip to a second axial velocity that is less than the first axial velocity; and the at least one flow reducing feature comprises a plurality of apertures in the wall of the constant diameter section such that a portion of a fluid flowing in the longitudinal direction exits the body through the plurality of apertures.

22. The jetless intravenous catheter of claim 21, wherein the at least one flow reducing feature is configured to excite the Tollmien-Schlichting instability associated with a fluid flowing in the constant diameter section in the longitudinal direction at the first axial velocity.

23. The jetless intravenous catheter of claim 21, wherein the wall of the constant diameter section comprises a top surface and a diametrically opposed bottom surface and first and second diametrically opposed side surfaces that are each disposed between the top surface and the bottom surface, and wherein the plurality of apertures comprises at least one aperture in the top surface of the wall of the constant diameter section and at least one aperture in each of the first and second side surfaces of the wall of the constant diameter section, and wherein the bottom surface of the wall of the constant diameter section does not include an aperture.

* * * * *

UNITED STATES PATENT AND TRADEMARK OFFICE
CERTIFICATE OF CORRECTION

PATENT NO. : 9,884,166 B2
APPLICATION NO. : 13/574705
DATED : February 6, 2018
INVENTOR(S) : Howle et al.

Page 1 of 1

It is certified that error appears in the above-identified patent and that said Letters Patent is hereby corrected as shown below:

In the Specification

Column 12, Line 43: Please correct "distance dl" to read -- distance d1 --

Signed and Sealed this
Third Day of July, 2018

Andrei Iancu
*Director of the United States Patent and Trademark Office*